United States Patent [19]

Finn

[11] Patent Number: 4,484,893
[45] Date of Patent: Nov. 27, 1984

[54] AIR TURBINE HANDPIECE FOR DENTAL SCALING AND OTHER APPLICATIONS

[75] Inventor: Arnold H. Finn, Farmington, Conn.

[73] Assignee: Taco Products, Inc., Plainville, Conn.

[21] Appl. No.: 468,489

[22] Filed: Feb. 22, 1983

[51] Int. Cl.³ .............................................. A61C 1/07
[52] U.S. Cl. ..................................... 433/118; 433/29;
433/120; 433/122
[58] Field of Search ............... 433/116, 118, 119, 120,
433/122, 123, 126, 127, 128, 129, 224, 29, 75,
76, 102

[56] References Cited

U.S. PATENT DOCUMENTS

| Re. 29,687 | 7/1978 | Sertich | 433/120 |
|---|---|---|---|
| Re. 30,536 | 3/1981 | Perdreaux, Jr. | 433/119 |
| 837,423 | 12/1906 | Sargent | 433/127 |
| 1,966,446 | 7/1934 | Hayes | 433/119 |
| 2,714,890 | 8/1955 | Vang | 433/119 |
| 3,518,766 | 7/1970 | Burt | 433/119 |
| 3,758,951 | 9/1973 | Scrivo et al. | 433/29 |
| 3,811,190 | 5/1974 | Sertich | 433/118 |
| 3,897,134 | 7/1975 | Scrivo et al. | 433/29 |
| 3,956,826 | 5/1976 | Perdreaux, Jr. | 433/86 |
| 4,169,984 | 10/1979 | Parisi | 310/323 |
| 4,260,380 | 4/1981 | Nash | 433/119 |
| 4,289,486 | 9/1981 | Sargeant | 433/118 |
| 4,330,282 | 5/1982 | Nash | 433/118 |

FOREIGN PATENT DOCUMENTS 8200 1/1879 Fed. Rep. of Germany ...... 433/120

Primary Examiner—John J. Wilson

[57] ABSTRACT

An oscillatory handpiece for a tool bit includes a housing having therewith fluid driven turbine rotor having an eccentric connection to an oscillatable rod which is effectively supported only at the point of its eccentric connection. The handpiece also includes means in the housing along the length of the rod which limits the amount of its oscillation and prevents its rotation. A liquid supply tube is disposed within the rod and supplies liquid to the tool bit which is removably engageable at the front end of the oscillatable rod. Moreover, by control of the oscillation limiting means and selection of materials and dimensions for the rod, harmonic vibrations may be used to augment the eccentrically generated oscillation and thus enhance the motion of the tool bit.

18 Claims, 10 Drawing Figures

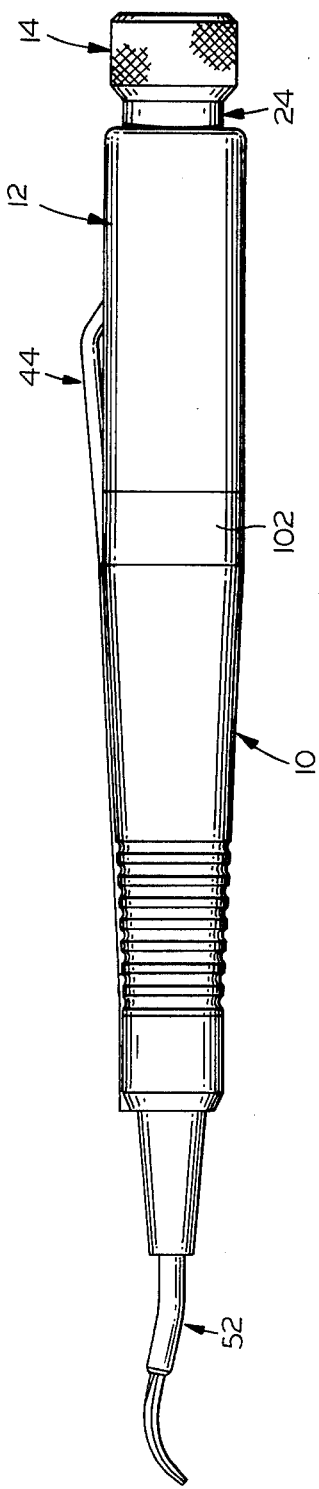
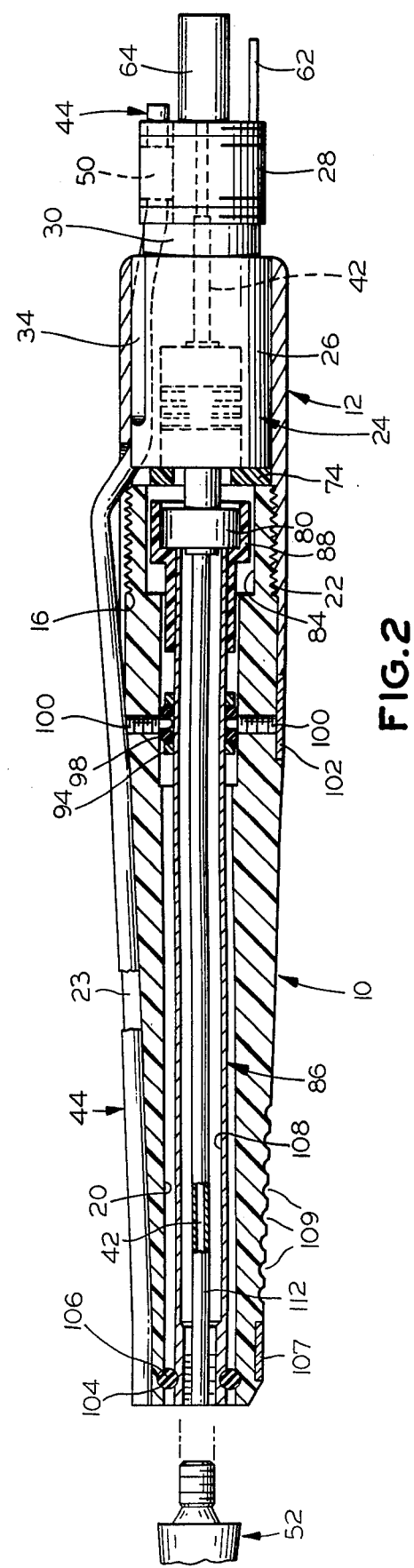

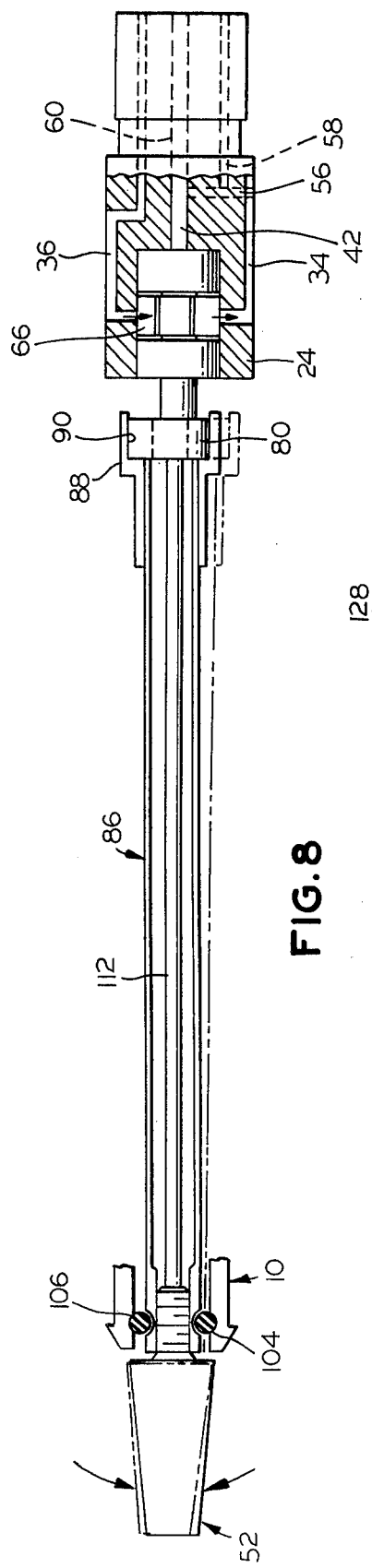
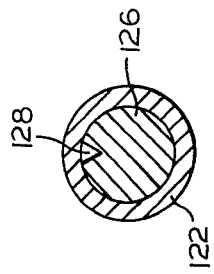
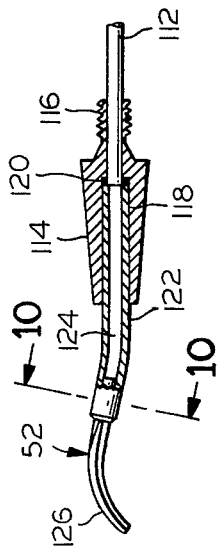
FIG. 8
FIG. 10
FIG. 9

AIR TURBINE HANDPIECE FOR DENTAL SCALING AND OTHER APPLICATIONS

BACKGROUND OF THE INVENTION

Handpieces for effecting oscillatory motion of a tool bit mounted therein are widely employed in dental, medical and crafts applications. Various mechanisms are used to convert rotary motion to oscillatory motion of the support for the tool bit, and various power sources are used to generate the initial rotary motion.

Air and water feed streams under pressure are preferred in the dental and medical field as the means for effecting the rotary motion of a turbine rotor, which rotary motion is converted to oscillation generally by some form of eccentric coupling to the tool bit supporting element. Such devices are widely and beneficially employed although various problems are encountered in their fabrication or use.

It is an object of the present invention to provide a novel handpiece for effecting oscillatory motion of a tool bit and which employs a long-lived and highly effective mechanism for converting rotary motion to oscillation of a rod supporting the tool bit.

It is also an object to provide such a handpiece wherein the components may be fabricated readily and relatively economically, and in which the components may be readily assembled and disassembled.

Another object is to provide such a handpiece which affords enhanced oscillatory motion of the tool bit and which exhibits long-lived and trouble-free operation.

SUMMARY OF THE INVENTION

It has now been found that the foregoing and related objects and advantages may be readily attained in a vibratory handpiece for effecting oscillatory motion of a tool bit which includes an elongated housing having a longitudinal passage opening at the front end thereof and a turbine chamber spaced from the front end. A fluid inlet is provided at the rear end of the housing for connection to a source of fluid under pressure. A fluid passage extends from the inlet to the periphery of the turbine chamber, and an exhaust passage extends from the turbine chamber to the exterior of the housing. Disposed in the turbine chamber is a turbine rotor which has a drive shaft extending therefrom in the passage towards the front end of the housing. Bearing means in the housing supports the drive shaft and thereby the turbine rotor for rotation within the housing.

An elongated oscillatable tubular rod extends in the housing passage from adjacent the end of the drive shaft to adjacent the front end of the housing. On the rear end of the rod adjacent the drive shaft is a cup member which has a recess receiving the end of the drive shaft, and the cup recess and drive shaft end cooperate to provide eccentric drive means to effect eccentric bearing action of the shaft end in the cup and thereby oscillatory motion of the rod. Means is provided in the passage of the housing to permit limited oscillatory movement of the rod therewithin while preventing relative rotation thereof. Since the rod is supported on the end of the drive shaft by the cup member so that it may oscillate along substantially its entire length. Lastly, the outer end of the rod has means thereon for releasable engagement therewith of an associated tool bit.

In the preferred embodiments, the rod is a lightweight tubular element, desirably having a relatively thin-walled tubular cross section and fabricated from a fatigue-resistant lightweight metal whereby high speed oscillatory motion of the rod produces concurrent harmonic vibration thereof.

The oscillation limiting means includes an O-ring in the passage adjacent the front end of the housing, and this O-ring has an inner diameter greater than the exterior dimension of the adjacent portion of the rod to provide clearance therebetween. The oscillation limiting means also includes a spring return mechanism in the passage intermediate the length of the rod. This mechanism includes resiliently deflectable means resiliently deflectable a limited distance by oscillation of the rod and biasing the rod to its at rest position. The resiliently deflectable means comprises a plurality of O-rings spaced about the circumference of the rod and having their axes normal to the axes of the rod and their outer faces spaced outwardly from the periphery of the rod.

In its preferred form the resiliently deflectable means includes a spring retainer secured on the rod and having recesses in its periphery seating a portion of the depth of the O-rings. Stop means on the housing extend into the center of the O-rings of the resiliently deflectable means to preclude rotation of the rod.

In the preferred devices, the rod and drive shaft are hollow, and the handpiece includes a liquid inlet and conduit means from the liquid inlet to the drive shaft for flow of liquid through the drive shaft and rod to the associated tool bit. The handpiece also includes a fiberoptic cable extending from adjacent the rear end of such housing to adjacent the front end thereof to illuminate the tip of an associated tool bit and the work area adjacent thereto. Desirably, a coaxially disposed cylindrical tube is provided within the end of the rod carried by the drive shaft, and the tube is spaced from the inner wall of the rod to define an annular cavity thereabout and provide the conduit for liqui7 d through the rod to the associated tool bit. The front end of the rod is internally threaded to provide the tool bit releasable engaging means.

In its most usual form, the eccentric drive means comprises a radially offset portion on the one end of the drive shaft and a generally annular bearing on the offset portion bearing against the inner surface of the cup member.

BRIEF DESCRIPTION OF THE DRAWINGS

FIG. 1 is a side elevational view of a handpiece embodying the present invention with a dental scraper bit assembled therein;

FIG. 2 is a fragmentary side elevational view of the handpiece of FIG. 1 drawn to an enlarged scale and partially in section, the tool bit being removed therefrom and fragmentarily illustrated, and the coupling nut being removed to illustrate the several conduits and fittings;

FIG. 8 is a partially diagrammatic sectional view of several of the operating elements of the handpiece showing the oscillatory motion;

FIG. 9 is a side elevational view in partial section of the dental bit of FIG. 1 with the water conduit fragmentarily illustrated as seated therein; and FIG. 10 is a sectional view of the bit along the line 10—10 of FIG. 9 and drawn to an enlarged scale.

DETAILED DESCRIPTION OF THE ILLUSTRATED EMBODIMENTS

Turning first to FIG. 1, therein illustrated is a dental handpiece embodying the present invention and having an external housing generally comprised of an elongated body member generally designated by the numeral 10, a bearing sleeve generally designated by the numeral 12, and a coupling nut generally designated by the numeral 14.

Figure 3:
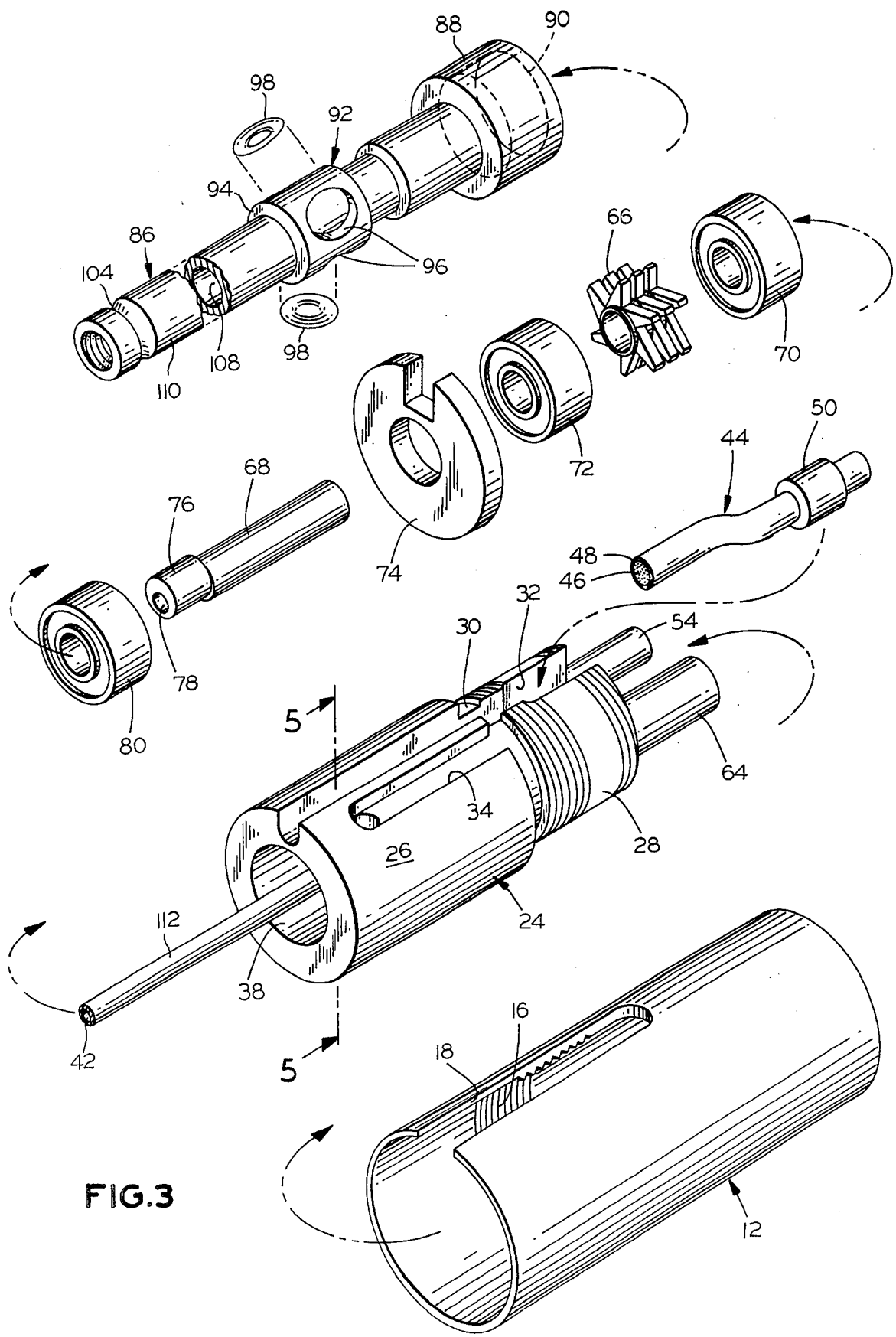
FIG. 3 is a practically exploded perspective view of the handpiece of FIGS. 1 and 2, omitting the tool bit, coupling nut and body member.

As seen in FIGS. 2 and 3, the bearing sleeve 12 has a generally tubular cross section with an internally threaded portion 16 and a slot 18 extending axially from its forward end. The body member 10 is of generally annular cross section providing an axial passage 20 therethrough and has an externally threaded inner end portion 22 which threadably engages with the threaded portion 16 of the bearing sleeve 12. Extending into the other end of the bearing sleeve 12 and press fit therewithin is the bearing housing generally designated by the numeral 24 and having a body portion 26 of generally annular cross section, a head portion 28 of reduced diameter which is externally threaded for engagement with the internally threaded coupling nut 14, and an intermediate neck portion 30 of still lesser diameter.

Figure 5:
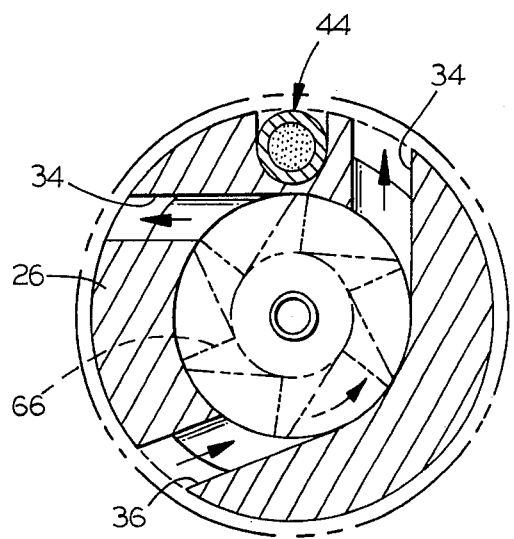
FIG. 5 is a cross sectional view to an enlarged scale of the handpiece along the line 5—5 of FIG. 3 with arrows diagrammatically showing air flow.
Figure 6:
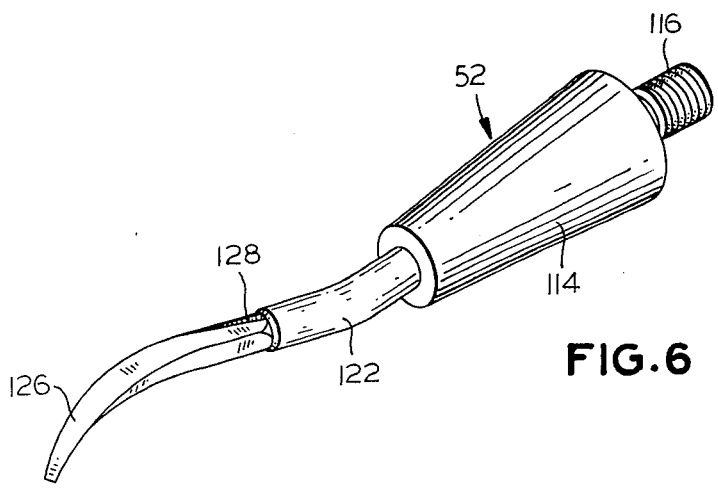
FIG. 6 is a perspective view to an enlarged scale of the dental scaler bit of FIG. 1.
Figure 7:
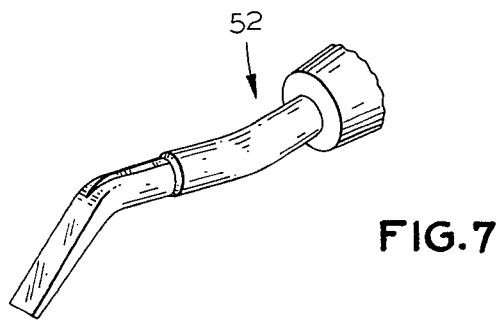
FIG. 7 is a fragmentary perspective view of another dental bit.

Extending axially in the outer surface of the bearing sleeve over its entire length is a channel 32 which registers with the slot 18 in the bearing sleeve 12. Spaced circumferentially from the channel 32 are a pair of exhaust channels 34 which extend axially in the outer surface of the body portion 26 from the rear end thereof and terminate at a point spaced from the front end thereof (only one of which is seen in FIG. 3). As seen in FIG. 8, an air feed passage 36 extends from the rear end of the bearing housing 24 and opens into the turbine chamber 38 at a point spaced from the exhaust openings 40 which communicate with the exhaust channels 34, all as best seen in FIGS. 5 and 8. Extending coaxially in the bearing housing 24 from the turbine chamber 38 to its rear end is a water passage 42.

The fiberoptic cable generally designated by the numeral 44 has a fiberoptic tube 46 and a protective metal sheath 48. It is formed into the configuration best seen in FIG. 2 and snugly seats in the groove 23 of the body member 10, and the bushing 50 thereon seats snugly in the channel 32 of the bearing housing 24. As seen in FIG. 2, the cable 44 terminates at the front end of the housing 10 so as to illuminate the end of the tool bit generally designated by the numeral 52.

Figure 4:
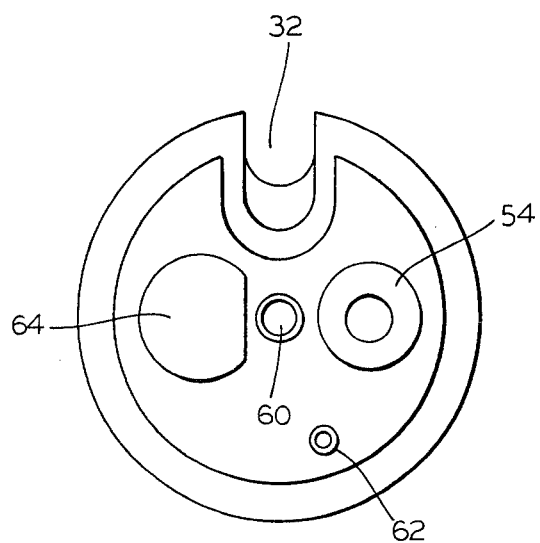
FIG. 4 is a rear end elevational view to an enlarged scale of the handpiece of FIG. 2.

Turning now to FIGS. 4 and 8, the rear end of the air feed passage 36 in the bearing housing 24 can be seen to have its rearward end enlarged to seat an inlet fitting 54 which projects rearwardly within the coupling nut 14. The water passage 42 has a radially extending section 56 which continues to the exterior of the bearing housing 24, and a radially offset axially extending portion 58 which terminates at the rear end of the bearing housing 24. There is also a coaxial bore 60 extending to the rear end of the bearing housing 24. Not shown are set screws which plug the outer ends of the bore 60 and radially extending section 56 to seal the passage 42 while permitting removal to effect cleaning of the passage 42. At the outer end of the axially extending section an enlarged portion seats a water inlet fitting 62 which projects into the coupling nut 14.

Also press fit into a bore in the rear end of the bearing housing is an axially extending post 64 which cooperates with the inlet fittings 54, 62 and fiberoptic cable 44 to effect alignment of the handpiece with the supply lines in the threaded connector (not shown) on the handpiece supply tubing (not shown) from the supply console (not shown).

Disposed in the turbine chamber 38 is a turbine rotor 66 having a multiplicity of vanes thereabout and rotatably supported on the drive shaft 68 which is seated in the bearings 70, 72 located on opposite sides of the turbine rotor 66. The drive shaft 68 extends through the spacer disc 74 and has a radially offset front end portion 76, best seen in FIG. 3, and a coaxial passage 78 extending therethrough which aligns with the water passage 42 in the bearing housing 24. The radially offset end portion 76 of the drive shaft 68 in turn carries the bearing 80 for the eccentric drive mechanism.

The body member 10 has a coaxial passage 20 extending therethrough with an enlarged portion 84 at the inner end thereof. Disposed within the passage 20 is the oscillatable tubular rod generally designated by the numeral 86, and secured on the inner end of the rod 86 in the enlarged passage portion 84 is the eccentric bearing cup 88 having a rearwardly facing recess 90 which snugly seats the outer periphery of the eccentric bearing 80. As can be seen, the outer diameter of rod 86 is considerably reduced from the diameter of the passage 20 so as to provide substantial annular spacing thereabout.

To prevent rotation of the rod 86 as a result of the eccentric rotation of the eccentric bearing 80 within the bearing cup 88, a spring retainer assembly generally designated by the numeral 92 is provided at a point spaced along the length of the rod 86 from the bearing cup 88. An annular spring retainer member 94 is fixed to the outer surface of the rod 86 and has a pair of diametrically spaced circular recesses 96 in its outer periphery in which are seated O-rings 98 of resiliently compressible material and of an axial thickness greater than the depth of the recesses 96 so that they project outwardly therefrom into contact with the inner wall of the body member 10 defining the passage 20. Set screws 100 are threadably and adjustably engaged in the wall of the body member 10 and have reduced diameter inner end portions extending into the central apertures of the O-rings 98 so that they function as stops to prevent rotation of the rod 86. The outer surface of the body member 10 is provided with a circumferential groove which seats the split ring 102 covering the several set screws 100.

Adjacent the outer end of the passage 20, the outer periphery of the rod 86 and the inner surface of the body member 10 are provided with aligned circumferential grooves 104 in which is disposed an O-ring 106 of resiliently compressible material. Although omitted in the drawings for ease of illustration, there is radial clearance between the surfaces of the grooves 104 and the O-ring. Thus, the O-ring 106 limits the amount of oscillation of the outer end portion of the rod 86. A split ring 107 extends about the outer periphery of the body member 10 to effect reinforcement thereof, and, as illustrated, circumferential ribs 109 on the exterior surface of the body member 10 facilitate gripping of the handpiece by the user.

The rod 86 is a tubular, thin-walled member having a passage 108 extending axially therethrough with the wall at outer end portion 110 being of greater thickness and internally threaded. Extending coaxially within the passage 108 is the water supply tube 112 which has its inner end seated in the water passage 78 in the offset end portion 76 of the drive shaft 68.

As seen in FIGS. 9 and 10, the tool bit 52 has a body element 114 with a threaded shank 116 which will threadably engage in the threaded end portion 110 of the oscillatable rod 86. A passage 118 extends axially therethrough, and a bushing seal 120 is provided intermediate the length thereof and in which the outer end of the water supply tube 112 seats to provide a seal.

Mounted in the front portion of the passage 118 is the mounting tube 122 which has the working tip 126 seated in the outer end of the passage 124 therethrough. As best seen in FIG. 10, the upper surface of the tip 126 has an axial groove 128 therein which communicates with the passage 124 of the tube 122 so that fluid will discharge over the surface of the tip 126.

In operation of the illustrated embodiment, the supply tubing from the console (not shown) is engaged with the coupling nut 14. Pressurized air entering through the inlet fitting 54 passages through the air feed passage 36 and is discharged into the turbine chamber 38 where it impinges upon the vanes of the turbine rotor 66 to effect rapid rotation thereof. The air flows through the chamber 38 and exits through the exhaust openings 40 into the exhaust channels 34 in which it flows rearwardly until discharged to the atmosphere at the rearward end of the body portion 26 of the bearing housing 24.

The rotation of the turbine rotor 66 and of its drive shaft 68 produces rotation of the eccentric bearing 80 in the recess 90 of the bearing cup 88, and this causes the oscillatable rod 86 to oscillate since it is prevented from rotation by the set screws 100 which extend into the O-rings 98 of the spring retainer assembly 98. Because the rod 86 is supported in cantilever fashion by the drive shaft 68, it is free to oscillate over substantially its entire length, causing limited resilient compression of the O-rings 98 of the spring retainer assembly 98 and some impacting upon the O-ring 106 at the front end of the body member 10 at the extremes of its oscillatory motion. Moreover, since the rod is fabricated from lightweight tubular stock, rapid oscillation appears to induce harmonic vibration in the rod 86 to provide enhanced oscillatory motion of the tool bit 52 carried thereby.

During use of the handpiece, water is introduced thereinto through the water inlet fitting 62 and flows through the water passage 42 into the passage 78 through the drive shaft 68 and thence through the water supply tube 112 to the tool bit 52 where it discharges through the groove 128 onto the surface of the tip 126 and over the work surface.

Light rays pass through the fiberoptic cable 44 and exit at the front end of the handpiece to illuminate the end of the tool bit 52 and the work area adjacent thereto.

By adjusting the spacing between the inner ends of the set screws 100 and the periphery of the oscillatable rod 86, the amount or distance the rod may oscillate at that point can be varied. It appears that having a smaller clearance at one of the three set screws 100 to produce some eccentricity in the direction of oscillation relative to the axis of the rod 86 at rest, causes greater or a higher frequency of oscillation, apparently due to harmonic vibration of the rod 86.

Exemplary of the dimensions and construction of components of a handpiece found highly effective are the following. The main body has an inner diameter of 0.265 inch, and the oscillatable rod has an outer diameter of 0.187 inch and an inner diameter of 0.156 inch. The rod is fabricated from aluminum alloy (6061 T6) and has a length of 2.86 inches forwardly of the bearing cup thereon. The O-rings of the spring retainer have a thickness of 0.062 inch and project about 0.003–0.005 inch from the surface of the spring retainer member and are compressible a total of about 0.003–0.005 inch diametrically of the rod. The O-ring at the outer end of the rod has an outer diameter of 0.312 inch and an inner diameter of 0.192 inch with the cooperating grooves providing a diametrical clearance of about 0.005 inch between the outer surface of the rod and the O-ring.

The various components of the assembly may be fabricated readily by molding and/or machining processes. Generally materials providing durability and resistance to corrosion are preferred, and lightweight, fatigue-resistant metal should be used for the oscillatable rod.

Conveniently, acetal, polyamide, and polycarbonate resins are employed for molding the bearing cup, body member, spacer, and bearing housing; passages and other internal formations may be readily machined therein. For strength and resistance to corrosion, stainless steel is desirably employed for the water tube, drive shaft, inlet fittings and cutting tip of the tool bit. Aluminum alloys are preferred for fabricating the bit body, spring return element, split rings and bearing housing.

The fiberoptic cable is conveniently an acrylic or polycarbonate resin rod encased in an stainless tube. The bearings are desirably corrosion resistant bearing assemblies which may have the individual race elements press fit or adhered to their respective members so as to rotate therewith.

As previously indicated, the oscillatable rod is to be fabricated from a lightweight, fatigue-resistant metal alloy such as tempered aluminum. Tests to date have indicated the suitability of 6061-T6 aluminum alloy. Moreover, the rod should have a relatively thin wall section over the major portion of its length to increase its flexural characteristics. Some experimentation as to the parameters of unsupported length, diameter and wall thickness may be desirable to superimpose apparent harmonic vibration at high speeds upon the oscillatory motion thereof.

As will be appreciated, the illustrated embodiment may be readily disassembled for cleaning or for replacement of worn parts. Moreover, it may be readily assembled from components which may be readily fabricated to close tolerances. In use, the handpieces have exhibited trouble-free and long-lived operation.

Although the handpiece of the present invention has been illustrated and described for use with air as the source of the pressurized stream to drive the turbine rotor, it will be appreciated that a pressurized water stream may be used as the power source.

Thus, it can be seen from the foregoing detailed description and attached drawings that the handpiece of the present invention provides high speed, controlled oscillation of readily interchangeable tool bits. The handpiece may be readily assembled from relatively simple and easily fabricated parts, and exhibits long-lived and trouble-free operation.

Having thus described the invention, I claim:

1. In a vibratory dental and medical handpiece for effecting oscillatory motion of a tool bit, the combination comprising:
   A. an elongated housing having a longitudinal passage opening at the front end thereof and a turbine chamber spaced from said front end, a fluid inlet at the rear end for connection to a source of fluid under pressure, a fluid passage from said inlet to the periphery of said turbine chamber, and an exhaust passage from said turbine chamber to the exterior of said housing;
   B. a turbine rotor in said turbine chamber and having a drive shaft extending therefrom in said passage towards said front end of said housing;
   C. bearing means in said housing supporting said drive shaft and therby said turbine rotor for rotation within said housing;
   D. an elongated oscillatable tubular rod in said passage extending from adjacent the end of said drive shaft to adjacent said front end of said housing, said rod being a lightweight tubular element of relatively thin-walled tubular cross section and fabricated from a fatigue-resistant lightweight metal whereby high speed oscillatory motion of said rod produces concurrent harmonic vibration thereof;
   E. a cup member on the rear of said rod adjacent said drive shaft and having a recess therein receiving the end of said drive shaft, said cup recess and said drive shaft end cooperating to provide eccentric drive means to effect eccentric bearing action of said shaft end in said cup and thereby oscillatory motion of said rod;
   F. means in said passage of said housing permitting limited oscillatory movement of said rod therewithin while preventing relative rotation thereof, said rod being supported on said end of said drive shaft by said cup member so that it may oscillate along substantially its entire length, said rotation preventing means permitting radial movement of said rod in said passage so as to permit said harmonic vibration thereof over the major portion of its length without substantial damping thereof;
   G. means at the other end of said rod for releasable engagement therewith of an associated tool bit.

2. The handpiece in accordance with claim 1 wherein said oscillation limiting means includes an O-ring in said passage adjacent said front end of said housing, said O-ring having an inner diameter greater than the exterior dimension of the adjacent portion of said rod to provide clearance therebetween.

3. The handpiece in accordance with claim 1 wherein said oscillation limiting means includes a spring return mechanism in said passage intermediate the length of said rod, said mechanism including resiliently deflectable means resiliently deflectable a limited distance by oscillation of said rod and biasing said rod to its at rest position.

4. The handpiece in accordance with claim 3 wherein said resiliently deflectable means comprises a plurality of O-rings spaced about the circumference of said rod and having their axes normal to the axis of said rod and their outer face spaced outwardly from said periphery of said rod.

5. The handpiece in accordance with claim 4 wherein said resiliently deflectable means includes a spring retainer secured on said rod and having recesses in its periphery seating a portion of the depth of said O-rings.

6. The handpiece in accordance with claim 5 wherein said oscillation limiting means includes stop means on said housing extending into the center of said O-rings of said resiliently deflectable means to preclude rotation of said rod.

7. The handpiece in accordance with claim 6 wherein said oscillation limiting means includes an O-ring in said passage adjacent said front end of said housing having an inner diameter greater than the exterior dimension of the adjacent portion of said rod to provide clearance therebetween.

8. The handpiece in accordance with claim 1 wherein said rod and said drive shaft are hollow and wherein said handpiece includes a liquid inlet and conduit means from said liquid inlet to said drive shaft for flow of liquid through said drive shaft and rod to the associated tool bit.

9. The handpiece in accordance with claim 1 wherein said handpiece includes a fiberoptic cable extending from adjacent said rear end of said housing to adjacent said front end thereof to illuminate the tip of an associated tool bit and the work area adjacent thereto.

10. The handpiece in accordance with claim 9 wherein said handpiece includes a coaxially disposed cylindrical tube within said rod end carried at one end by said drive shaft, said tube being spaced from the inner wall of said rod to define an annular cavity thereabout and providing the conduit for liquid through said rod to the associated tool bit.

11. The handpiece in accordance with claim 1 wherein the other end of said rod is internally threaded to provide said tool bit releasable engaging means.

12. The handpiece in accordance with claim 1 wherein said eccentric drive means comprises a radially offset portion on said one end of said drive shaft and a generally annular bearing on said offset portion bearing against the inside surface of said cup member.

13. In a vibratory dental and medical handpiece for effecting oscillatory motion of a tool bit, the combination comprising:
   A. an elongated housing having a longitudinal passage opening at the front end thereof and a turbine chamber spaced from said front end, a fluid inlet at the rear end for connection to a source of fluid under pressure, a fluid passage from said inlet to the periphery of said turbine chamber, and an exhaust passage from said turbine chamber to the exterior of said housing;
   B. a turbine rotor in said turbine chamber and having a drive shaft extending therefrom in said passage towards said front end of said housing, said drive shaft having a radially offset portion at its front end and a bearing on said offset portion;
   C. bearing means in said housing supporting said drive shaft and thereby said turbine rotor for rotation within said housing;
   D. an elongated oscillatable lightweight tubular rod in said passage extending from adjacent the front end of said drive shaft to adjacent said front end of said housing, said rod being a lightweight tubular element of relatively thin-walled tubular cross section and fabricated from a fatigue-resistant lightweight metal whereby high speed oscillatory motion of said rod produces concurrent harmonic vibration thereof;

E. a cup member on the rear end of said rod adjacent said drive shaft and having a recess therein receiving the end of said drive shaft, said cup recess receiving said bearing on said offset portion of said drive shaft to provide eccentric drive means and thereby oscillatory motion of said rod;

F. means in said passage of said housing permitting limited oscillatory movement of said rod therewithin while preventing relative rotation thereof, said rod being supported on said end of said drive shaft by said cup member so that it may oscillate along substantially its entire length, said rotation preventing means permitting radial movement of said rod in said passage so as to permit said harmonic vibration thereof over the major portion of its length without substantial damping thereof;

G. means at the other end of said rod for releasable engagement therewith of an associated tool bit.

14. The handpiece in accordance with claim 13 wherein said oscillation limiting means includes a spring return mechanism in said passage intermediate the length of said rod, said mechanism including a plurality of resiliently deflectable O-rings spaced about the circumference of said rod and having their axes normal to the axis of said rod and their outer face spaced outwardly from said periphery of said rod, said O-rings being resiliently deflectable a limited distance by oscillation of said rod and biasing said rod to its at rest position, and said mechanism further including a spring retainer secured on said rod and having recesses in its periphery seating a portion of the depth of said O-rings.

15. The handpiece in accordance with claim 14 wherein said oscillation limiting means includes stop means on said housing extending into the center of said O-rings of said resiliently deflectable means to preclude rotation of said rod.

16. The handpiece in accordance with claim 15 wherein said oscillation limiting means includes an O-ring in said passage adjacent said front end of said housing having an inner diameter greater than the exterior dimension of the adjacent portion of said rod to provide clearance therebetween.

17. The handpiece in accordance with claim 13 wherein said rod and said drive shaft are hollow, wherein said handpiece includes a coaxially disposed cylindrical tube within said rod and carried at one end by said drive shaft, said tube being spaced from the inner wall of said rod to define an annular cavity thereabout and providing a conduit for liquid through said rod to the associated tool bit, and wherein said handpiece includes a liquid inlet and conduit means from said liquid inlet to said drive shaft for flow of liquid through said drive shaft and rod to the associated tool bit, and wherein said handpiece additionally includes a fiberoptic cable extending from adjacent said rear end of said housing to adjacent said front end thereof to illuminate the tip of an associated tool bit and the work area adjacent thereto.

18. The handpiece in accordance with claim 13 wherein the other end of said rod is internally threaded to provide said tool bit releasable engaging means.

* * * * *